US00PP30477P2

(12) United States Plant Patent
Hansen

(10) Patent No.: US PP30,477 P2
(45) Date of Patent: May 7, 2019

(54) ***VERONICA* PLANT NAMED 'MONA LISA SMILE'**

(50) Latin Name: ***Veronica spicata* L.**
Varietal Denomination: Mona Lisa Smile

(71) Applicant: Hans A Hansen, Zeeland, MI (US)

(72) Inventor: Hans A Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 15/932,165

(22) Filed: Feb. 14, 2018

(51) Int. Cl.
*A01H 6/68* (2018.01)

(52) U.S. Cl.
USPC ..... Plt./251

(58) Field of Classification Search
USPC ..... Plt./251
CPC ..... A01H 6/68; A01H 5/02
See application file for complete search history.

*Primary Examiner* — Keith O. Robinson

(57) ABSTRACT

The new and distinct cultivar of ornamental spike speedwell plant, *Veronica* 'Mona Lisa Smile', with upright mounded habit of well-branched branched spikes producing rosy-purple flowers over a long period beginning late spring. The new plant is useful in the landscape as an accent plant, en masse, as a container plant, or cut flower.

2 Drawing Sheets

Botanical classification: *Veronica spicata* L.
Variety denomination: 'Mona Lisa Smile'.

BACKGROUND OF THE INVENTION

The present invention relates to the new and distinct cultivar of spike speedwell, botanically known as *Veronica spicata* 'Mona Lisa Smile', and hereinafter referred to as the cultivar 'Mona Lisa Smile' or the "new plant". The new plant was hybridized in the summer of 2012 by the inventor at a wholesale perennial nursery in Zeeland, Mich., USA, with the proprietary unreleased hybrid known only as 08-64-01B (not patented) as the female parent and 'Rotfuchs' (also known as 'Red Fox') (not patented) as the male parent. The cross was performed on Jun. 29, 2012 and the individual seedling that was ultimately named 'Mona Lisa Smile' was identified by the breeder code 12-27-04 throughout the trial period. The seeds were planted on Dec. 12, 2012.

The new plant has been asexually propagated by shoot tip cuttings at the same nursery in the greenhouses in Zeeland, Mich., since the summer of 2014 with subsequent asexually propagated plants found to be identical to the original selection with all the same traits as the original seedling.

No plants of *Veronica* 'Mona Lisa Smile' have been sold or disclosed by this or any other name, in this country or anywhere in the world, prior to one year from the filing of this application, except that which was sold or disclosed within one year of the filing of this application and which was either derived directly or indirectly from the inventor.

BRIEF SUMMARY OF THE PLANT

*Veronica spicata* 'Mona Lisa Smile' is unique from all other spike speedwell known to the inventor. Several other cultivars may have some similar traits, but this is the only variety known by the inventor to have the following characteristic combinations that establish the new plant as unique:

1. Upright mounded habit of well-branched spikes above the foliage;

2. Flowering is very early, beginning early to mid-June in Michigan;
3. Long spikes of rosy-purple colored flowers;
4. Freely branched peduncles with long blooming season.

The closest comparison cultivars known to the inventor are 'Baby Doll' U.S. Plant Pat. No. 16,428 and the male parent 'Red Fox'. The new plant is taller, wider in habit with less reddish coloration in the flower than 'Red Fox'. 'Baby Doll' has a less branched habit with soft pink-colored flower colors. Compared with 'Pink Potion' U.S. Plant Pat. No. 29,681 is more compact and shorter in height. 'Perfectly Picasso' U.S. Plant Pat. No. 29,720 is slightly taller with longer spikes of medium pink flowers. Compared with the female parent the new plant is taller and has darker flowers.

BRIEF DESCRIPTION OF THE DRAWINGS

The photograph of the new plant demonstrates the overall appearance and unique traits of 'Mona Lisa Smile' as a three-year-old plant grown in a full-sun trial garden in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
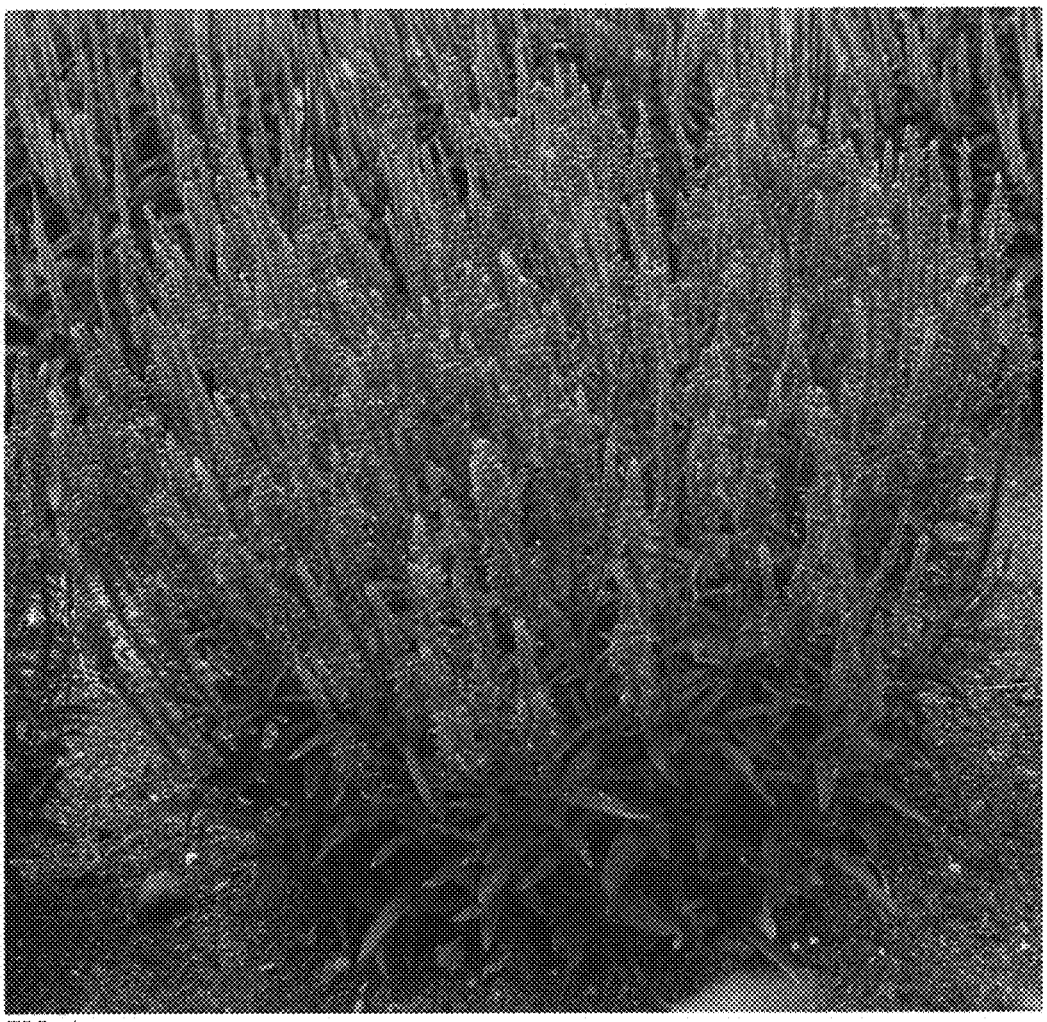
FIG. 1 shows the habit of the new plants in full flower.
Figure 2:
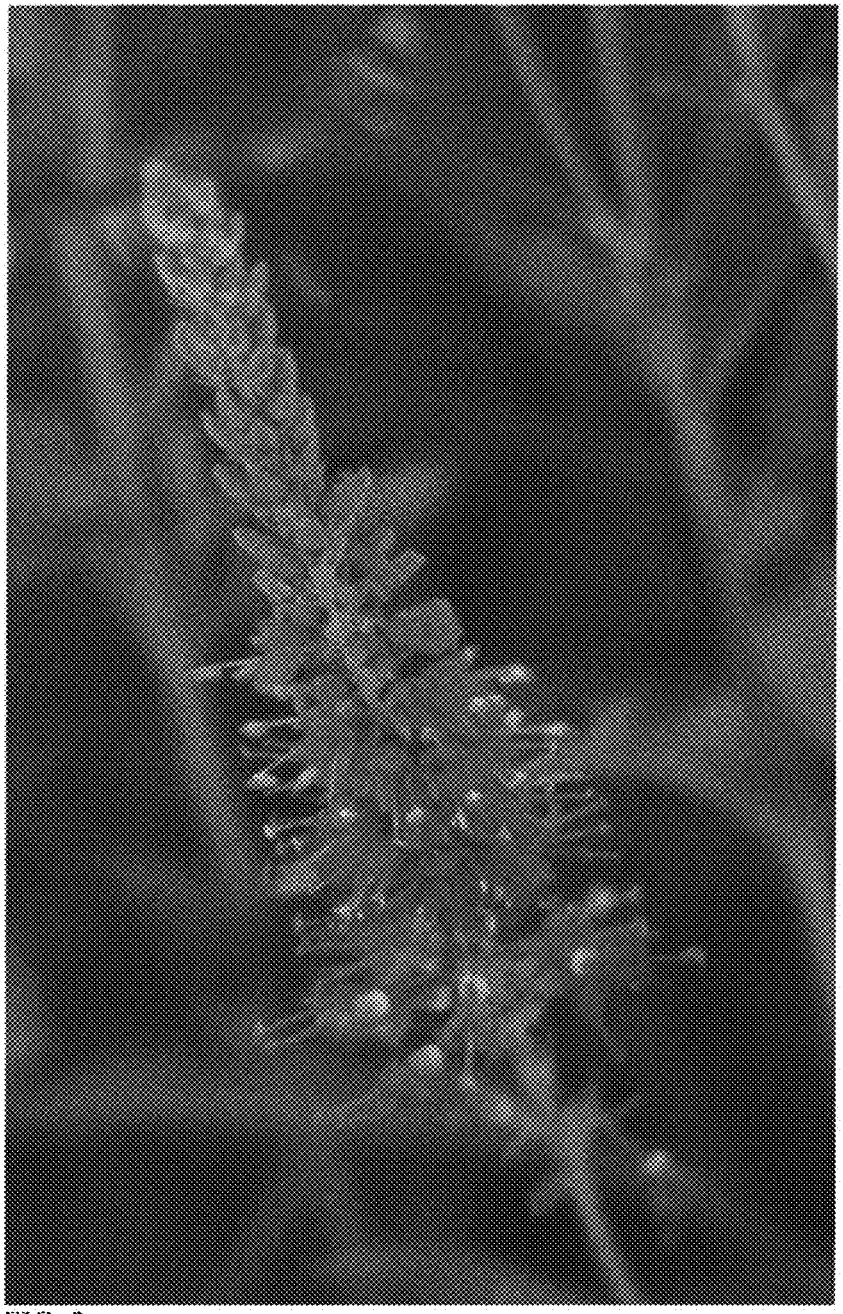
FIG. 2 shows a close-up of the flowers and buds.

The following descriptions and color references of *Veronica* 'Mona Lisa Smile' are based on the 2001 edition of The Royal Horticultural Society Colour Chart except where common dictionary terms are used. *Veronica* 'Mona Lisa Smile' has not been observed under all possible environments. The phenotype may vary slightly with different growing environments such as temperature, light, fertility, soil pH, moisture and maturity levels, but without any change in the genotype. The following observations and size descriptions are based on three-year old plants in the full sun trial garden of a nursery in Zeeland, Mich. with supplemental fertilizer and water as needed.

Botanical classification: *Veronica spicata;*

Parentage: The female (seed parent) was the proprietary hybrid known by the breeder code 08-64-01B; the male (pollen parent) was *Veronica* 'Red Fox';

Plant habit: Hardy herbaceous perennial, with average 30 highly-branched stems, main stems blooming to about 60.0 cm tall and clumping to about 56.0 cm across; flowering beginning early June in Michigan and continuing for about 4 weeks with occasional repeat if deadheaded;

Leaves: Simple, flat, elliptic to lanceolate; opposite; serrated margin with about 3 teeth per one centimeter; glabrous below and above, acute apex, attenuate base;

Leaf size: About 6.5 cm long by 1.5 cm wide decreasing in both length and width distally;

Leaf color: Mature leaves adaxial between RHS 137A and RHS 139A, mature abaxial nearest RHS 137C; young expanding leaves nearest RHS 144A adaxial and abaxial;

Veins: Reticulate, abaxial puberulent and glabrate to glabrous adaxial; abaxial midrib costate, about 1.0 mm across at abaxial base and about 0.5 mm at adaxial base;

Vein color: Adaxial midrib nearest RHS 147D and secondary veins between RHS 137A and RHS 139A; abaxial midrib nearest RHS 147D with secondary veins nearest RHS 137A;

Petiole: Simple; slightly concaved upward on edges; margin ciliolate; about 1.5 cm long and 4.0 mm wide length, shorter and narrower on distal leaves;

Petiole color: Adaxial base nearest RHS 144D, distally between RHS 137A and RHS 139A; abaxial nearest RNS 144D;

Buds one to two days prior to opening: Convolute, narrowly oblong, obtuse apex; about 5.5 mm long and 2.5 mm diameter;

Bud color: Between RHS 64B and RHS 64C throughout;

Flowers: On heavily branched upright spikes in compressed conglomerate; numerous; zygomorphic; campanulate; approximately 300 per main spike; about 8.0 mm long and about 7.0 mm across; flowers persist individually for 4 to 6 days whether on the plant or cut; petals self-cleaning, sepals and style persistent;

Flower attitude: Outwardly;

Flower timing: Early to mid-summer and repeating if deadheaded into early fall;

Flower fragrance: None detected;

Petals: Four; one larger petal above and three slightly smaller below and to either side; simple, entire, fused in basal 2.5 mm; glabrous abaxial and pubescent with 1.0 mm long hairs in tuft band about 1.0 to 2.0 mm from adaxial base; upper larger petal with rounded apex, about 5.5 mm long by 2.0 mm wide; side and lower petals with acute apex, about 5.5 mm long and 1.5 mm wide;

Petal color: Abaxial nearest RHS 64C and adaxial nearest RHS 64C, pubescent adaxial tube white nearest RHS NN155D;

Androecium:

*Filaments*.—Two; divergent; glabrous; epipetalous about 1.0 mm from base; about 5.5 mm long by about 0.25 mm diameter; color nearest RHS N74C.

*Anther*.—Dorsifixed, longitudinal; elliptic with acute apex and rounded base; about 1.5 mm by 1.0 mm; color nearest RHS 75C proximally and nearest RHS NN74D distally.

*Pollen*.—Abundant, globose, less than 0.1 mm; nearest RHS 8D.

Gynoecium: Single, superior; persists after petal drop;

*Style*.—Straight; attitude mostly outwardly; about 7.0 mm long and 0.25 mm diameter; color RHS N74C.

*Stigma*.—Globose; finely puberulent; about 0.3 mm in diameter; color RHS 75D.

*Ovary*.—Spherical to slightly elliptic; about 1.0 mm long and 0.8 mm in diameter; color nearest RHS 145B.

Sepals: Four, surface dull, ovate to narrowly ovate, acute apex, base fused forming campanulate calyx, puberulent margin; adaxial glabrous; abaxial nearly microscopically puberulent; about 3.0 mm long and 1.0 mm across;

Sepal color: Abaxial and adaxial between RHS 138A and RHS N138B;

Peduncle: Strong, erect, branched at nodes; terete; puberulent; about 25.0 cm long and 2.5 mm in diameter at the base; terminal flowering section of the main stem 10 to 12 cm long; attitude upwardly; freely branching at nodes; about 6 to 7 nodes before flowers; average internode length about 1.5 cm;

Peduncle color: Blend between RHS 146A and RHS 137C;

Pedicel: Rigid, about 1.0 mm long and 0.3 mm wide, finely puberulent; attitude mostly outwardly;

Pedicel color: Between RHS N138B and RHS 138A;

Bract: One, subtending each flower; linear; acute apex; entire; sessile; based fused to peduncle; proximal bracts about 6.5 cm long and 1.0 mm wide, decreasing in size distally;

Bract color: Adaxial between RHS 137A and RHS 139A, and abaxial between RHS 137C and RHS 138A;

Fruit: Ellipsoid, about 3.0 mm long and 2.5 mm across; color between RHS 166A and RHS 166B;

Propagation: The plant roots from cuttings in about 2 weeks and finishes to flowering in a 3.8 liter container in 8 to 10 weeks following a vernalization period of about 8 weeks;

Hardiness, pest and disease resistance: The plant grows best with plenty of moisture and adequate drainage, but is able to tolerate some drought when mature. Hardiness at least from USDA zone 4 through 9. Disease and pest resistance beyond what is typical of that of other spike speedwell has not been observed.

It is claimed:

1. A new and distinct cultivar of ornamental spike speedwell plant, *Veronica* 'Mona Lisa Smile', as herein described and illustrated.

* * * * *